United States Patent [19]

Bochskandl

[11] 4,416,901
[45] Nov. 22, 1983

[54] PROCESS FOR PROLONGING THE SHELF LIFE OF COSMETICS

[75] Inventor: Margarete Bochskandl, New York, N.Y.

[73] Assignee: American Frometics, Inc., New York, N.Y.

[21] Appl. No.: 325,945

[22] Filed: Nov. 30, 1981

[51] Int. Cl.$^3$ .................. A61K 47/00; A61K 35/78
[52] U.S. Cl. ................................ 424/363; 424/168;
   424/195; 424/284; 424/359; 424/359; 424/364;
   424/365
[58] Field of Search ............... 424/365, 168, 364, 363

[56] References Cited

FOREIGN PATENT DOCUMENTS 55-62005  5/1980  Japan .................................. 424/364
1337461  11/1973  United Kingdom ................ 424/364

OTHER PUBLICATIONS

Chem. Abs. 1978, vol. 88, 177052m.
Pharmaceutical Sciences, Remington's, 1975, 15th Ed. pp. 1389 to 1393.

Primary Examiner—Dale R. Ore
Attorney, Agent, or Firm—Ladas & Parry

[57] ABSTRACT

Cosmetic products are subjected to pasteurization by heating at pasteurization temperatures, then to deep freezing at temperatures below −100° C. and storage at −40° C. to increase the shelf life of the products and to eliminate most of the microorganisms.

11 Claims, No Drawings

PROCESS FOR PROLONGING THE SHELF LIFE OF COSMETICS

BACKGROUND OF THE INVENTION

The present invention generally deals with prolonging the shelf life and the period of resistance against microorganisms of cosmetic products.

The cosmetic industry has long been concerned about preventing deterioration and prolonging the shelf life of cosmetics. On prolonged use, a cosmetic is subject to change in its activity, may become unstable or may separate into its ingredients.

Known methods to overcome these difficulties require the incorporation of bacteriostatic agents as preservatives and antioxidants to limit autoxidation or involve costly procedures such as preparation of the cosmetic formulations in a vacuum. The preservatives used in the prior art are often inadequate in preventing microbial and fungal action on naturally occurring substances incorporated in a cosmetic product. These products are therefore overloaded with preservatives. Cosmetics infested with fungi or other microorganisms when applied continuously to the skin may cause local infections especially where slight abrasions or cuts are present.

Many preservatives become chelated or sequestrated from the lipophilic phase of the emulsifier so affecting the stability and sterility of the cosmetics.

The antioxidants used in cosmetics have a limited active life. They can be used only in small quantities since they irritate the skin as has been described in scientific publication on allergies and other skin problems.

Particularly the activity of naturally occurring active ingredients in the cosmetic products such as vitamins and hormones is significantly reduced through these conventional cosmetic preparations.

BRIEF SUMMARY OF THE INVENTION

According to the invention a process for prolonging the shelf life and period of resistance to microorganisms of cosmetics in the form of emulsions, suspensions or solutions is provided comprising:
(a) packing said cosmetic in airtight containers under vacuum or inert gas (nitrogen) atmosphere,
(b) subjecting said packed cosmetic to pasteurization by heating to a temperature of from about 62° C. to about 75° C. until the center of the product has been exposed to said temperature for at least about 20 minutes and
(c) deep freezing said pasteurized cosmetic to a temperature of below about −100° C.
(d) holding said treated product for at least about 45 days, generally at about −40° C. or lower, and
(e) maintaining at low temperatures of −20° C. or less.

The invention is particularly advantageous with respect to cosmetics the active parts of which consist solely of natural products since such natural products are more easily subject to deterioration and are therefore more difficult to preserve. Natural products are defined in the context of the invention as substances which are found in unchanged form in nature or substances which are part of a natural material and are separated therefrom e.g. by boiling, extraction, filtration, coalescence etc. However, any cosmetic containing material subject to deterioration from microorganisms will benefit from the present process.

Once packed in vacuum or inert gas atmosphere, the pasteurization is at temperatures from about 60° C. to about 75° C. e.g. at 63° C. which is the usual pasteurization temperature of milk. The pasteurization time is at least 20 minutes and may range from about 40 to 50 minutes or more depending on the heat penetration factor into the emulsion.

The deep freezing step of the present process is at a temperature below about −100° C.

The product formed according to the invention is generally preserved at −40° C. for at least 45 days but this temperature and time is not critical and may vary.

As suggested above, a cosmetic formulation generally includes a cosmetically active part e.g. fruit extracts, herbal extracts vegetable or animal oils, hormones etc. The remainder is the base or carrier which contain non-naturally occurring (synthetic) materials.

It was found that the present process increased the shelf life and prolonged the resistance against microorganisms of cosmetics as will be shown below on the basis of tests performed on cosmetics treated according to the invention.

The cosmetic formulations are generally prepared following certain manufacturing and sanitary procedures. All raw materials are checked for absence of microbial contamination before use. Tanks, homogenizers and other manufacturing equipment coming into contact with the ingredients of the cosmetic product are washed with hot detergent solution, rinsed, sanitized with an antiseptic such as a chlorine solution and again rinsed before use. Until use all the above equipment must be covered after sanitation.

During the entire manufacturing process starting with phase combination and including overnight holding as described below a flow of nitrogen gas should preferably be maintained over the manufacturing tanks. The tubes to be filled with the end product and the filling equipment all are cleaned and sanitized prior to filling. During filling, the tubes and formulations are protected from contamination again by a continuous flow of nitrogen or other inert gas.

The pasteurization is while the cosmetic product is in the tube under vacuum or inert gas. The filled tubes are then formed into frozen loads and these are immediately quick frozen using a liquid nitrogen quick freezer. The contents are preferably cooled to −100° C. to −120° C. in as short a period of time as practically possible and held at this temperature until the center of the product is exposed to this temperature for generally at least 12 minutes. The product is then put into cold storage at about −40° C. generally for 45 days, and then preserved at low temperatures of about −20° C. The products can withstand multiple thawing and freezing cycles at about −20° C. both if opened and if not opened. Once opened and kept at room temperature the contents last without apparent microbiological growth for up to several months.

EXAMPLE 1

Day cream for dry skin

| No. | Phase | Ingredient | % by Weight |
|---|---|---|---|
| 1 | A | DEIONIZED WATER | 58.60 |
| 2 | A | GLYCERINE 96% NAT. | 10.00 |
| 3 | A | SODIUM CARBONATE | 0.80 |
| 4 | A | ALOE VERA EXTRACT | 0.10 |
| 5 | B | STEARIC ACID XXX | 7.00 |
| 6 | B | GENEROL 122 | 2.50 |
| 7 | B | RICE WAX No. 1 | 2.00 |
| 8 | B | NEO FAT 90-04 (armac) (Oleic Acid) | 0.50 |
| 9 | B | SUNFLOWER OIL | 6.00 |
| 10 | B | PEANUT OIL | 6.00 |
| 11 | B | SESAME OIL | 5.50 |
| 12 | B | VITAMIN E ACETATE | 0.10 |
| 13 | B | LIPOTROPHINA | 0.50 |
| 14 | C | COLLEGENONE | 0.10 |
| 15 | C | HERBAL EXTRACT 680 | 0.10 |
|  |  | 681 | 0.10 |
| 16 | D | PERFUME (SYNAROME) | 0.10 |
|  |  | TOTAL | 100.00 |

Phases A and B are heated separately to 80° C. B is added to A with agitation. After cooling to 50° C. phase C is added. Phase D is added after further cooling to 45° C. The mixture is left to stand overnight, is homogenized, and filled into tubes. The tubes are pasteurized by placement in a covered wire basket, immersing in water at 65° C. and holding at that temperature for 45 minutes.

The tubes after removal from the water bath are quick frozen to −100° C.

The pH of the cream is 7.5 and the viscosity 70.000 cps.

Lipotrophina M is a mixture of vitamins F and E, extract of egg yolk and carathenes (pro-vitamin A).

EXAMPLE 2

Night cream for dry skin.

| No. | Phase | Ingredient | % by Weight |
|---|---|---|---|
| 1 | A | BEESWAX BLEACHED | 8.00 |
| 2 | A | SESAME OIL | 8.00 |
| 3 | A | SOYBEAN OIL | 21.00 |
| 4 | A | PEANUT OIL | 15.00 |
| 5 | A | RICE BRAN OIL | 18.00 |
| 6 | A | LIPOTROPHINA A | 0.50 |
| 7 | A | MELABION | 0.20 |
| 8 | A | VITAMIN E ACETATE | 0.50 |
| 9 | B | DEIONIZED WATER | 27.61 |
| 10 | B | SODIUM BORATE | 0.40 |
| 11 | B | HERBAL EXTRACT 680 | 0.10 |
| 12 | B | HERBAL EXTRACT 681 | 0.10 |
| 13 | C | PERFUME 24-992 | 0.30 |
| 14 | D | CITRIC ACID H$_2$O (50%) | 0.29 |
|  |  | TOTAL | 100.00 |

The compoments of phase A are heated to 70° C. and the components of phase B are heated to 70° C. Phase B is slowly added to A with agitation and the mixture cooled. Phase C is added. After cooling to 45° C. phase D is added and the emulsion cooled to 30° C. The emulsion is homogenized and filled into tubes. Pasteurization of the filled tubes is as in Example 1. The pasteurized tubes are quick-frozen to −100° C.

The pH of the cream is 5.9–6.1 and the viscosity is 300.000 to 600.000 cps.

Melabion of the Tri-K Corporation is an extract of the entire honeycomb including the wax and the honey.

EXAMPLE 3

Day cream for oily skin

| No. | Phase | Ingredient | % by Weight |
|---|---|---|---|
| 1 | A | DEIONIZED WATER | 60.90 |
| 2 | A | GLYCERINE 96% NAT. | 10.00 |
| 3 | A | SODIUM CARBONATE | 1.00 |
| 4 | A | GUAR GUM MM (w) (Meer Corporation) | 0.20 |
| 5 | A | ALOE VERA EXTRACT | 5.00 |
| 6 | B | STEARIC ACID | 7.00 |
| 7 | B | GENEROL 122 (Henkel) | 1.50 |
| 8 | B | BEESWAX BLEACHED | 1.00 |
| 9 | B | RICE WAX NO. 1 | 1.00 |
| 10 | B | RICE BRAN OIL | 6.00 |
| 11 | B | SOY BEAN OIL | 6.00 |
| 12 | B | VITAMIN E ACETATE | 0.10 |
| 13 | C | COLLEGENONE | 0.10 |
| 14 | D | HERBAL EXTRACT 680 | 0.10 |
| 15 | E | PERFUME 16778 | 0.10 |
|  |  | TOTAL | 100.00 | pH 8.2—Viscosity 15,000 cps.

The guar gum is dispersed in the glycerine and added to the water. The balance of phase A is added and the mixture heated to 80° C. with agitation. Phase B is heated to 80° C. in a separate vessel. After slowly adding B to A with agitation, the mixture is cooled and phase C added. Phase D is added after cooling to 45° C. and the mixture allowed to stand overnight. After remixing, the emulsion is homogenized, filled into tubes, pasteurized as in Example 1 and immediately flash-frozen.

Generol 122 (Trade Mark) of Henkel is a refined grade of Phytosterol obtained from edible soybean oil. The product is a uniform blend of plant sterols consisting primarily of sitosterol, compesterol and stigmasterol.

Collegenone is a collegen protein which is an animal extract of the connective tissues of animals.

Perfume 16778 is obtained from natural ingredients according to a secret formula.

EXAMPLE 4

Cleansing cream for dry skin

| No. | Phase | Ingredient | % by Weight |
|---|---|---|---|
| 1 | A | BEESWAX BLEACHED | 8.00 |
| 2 | A | SESAME OIL | 8.00 |
| 3 | A | SOYBEAN OIL | 21.00 |
| 4 | A | PEANUT OIL | 15.00 |
| 5 | A | RICE BRAN OIL | 18.00 |
| 6 | A | VITAMIN E ACETATE | 0.50 |
| 7 | B | DEIONIZED WATER | 28.01 |
| 8 | B | SODIUM B ORATE | 0.40 |
| 9 | B | HERBAL EXTRACT 680 | 0.15 |
| 10 | B | HERBAL EXTRACT 681 (Meer Corporation) | 0.15 |
| 11 | C | PERFUME 4813 (Elias) | 0.50 |
| 12 | D | CITRIC ACID H$_2$O | 0.29 |
| 13 | E | GRAPESKIN EXTRACT | q.s. |

-continued

| Cleansing cream for dry skin | | | |
|---|---|---|---|
| No. | Phase | Ingredient | % by Weight |
| | | TOTAL | 100.00 |

The cream is manufactured as set out in Example 2, has a pH of 5.9–6.1 and a viscosity of 300.000 to 600.000 cps. Phase E is added together with phase D.

The following test procedures were followed to determine the extent of microbial contamination of the products prepared according to the process of the invention.

One gram of a test sample is dissolved in a dilution medium (TAT broth) consisting of fluid casein digest (trypticase), soy lecithin and polysorbate 20 (Tween 20), a de-emulsifier. The solution is diluted to 0.01 dilution and 1 ml. thereof is pipetted into each of two sterile Petri dishes. To each dish 15 to 20 ml of melted agar (soybeancasein digest agar medium) is added promptly. The plates are allowed to harden, inverted and incubated at 32° C. for 48 hours. After incubation, the number of colonies is counted. If no growth is observed, the result is expressed below as 0 per 0.1 g. The number of bacteria per gram of sample is obtained by multiplying the counted colonies by the dilution.

In the table below, the number 10 in the column under Total Plate Count (TPC) means less than 10 counts.

According to the Gram Stain procedure, isolated bacteria are stained with a mixture of dyes and observed microscopically to determine whether they are Gram positive (blue) or Gram negative (red). The most harmful bacteria are of the Gram negative type.

Table I shows the type of microbiological contamination of formulations produced according to the invention. The tests were performed on 12 tubes of each one of the four formulations. They give the same results for the formulations of Examples 1, 2, and 4 and the minimum and maximum counts for the formulation of Example 3.

TABLE I

| Total Plate Count (TPC) | Gram Stain (GS) Growth in 100 ml TAT broth 1/1g | Formulation of Example No. |
|---|---|---|
| 10 | No growth | 1 |
| 10 | No growth | 2 |
| 40–370 | Gram Negative Bacilli | 3 |
| 10 | No Growth | 4 |

After holding the samples tested above for two weeks at room temperature, the following results were obtained.

| TPC | GS | Example No. |
|---|---|---|
| 1,800,000 | Gram Negative Bacilli | 1 |
| 10 | No Growth | 2 |
| 190,000 | Gram Negative Bacilli | 3 |
| 10 | No Growth | 4 |

TABLE II

| Example 1 | Time period | TPC | GS |
|---|---|---|---|
| 1 | 2 weeks | 10 | No Growth |
| 1 | 3 weeks | 2,200,000 | Gram Negative Bacilli |
| 1 | 4 weeks | 10 | No Growth |
| 2 | 2 weeks | 10 | No Growth |
| 2 | 3 weeks | 10 | No Growth |
| 2 | 4 weeks | 10 | No Growth |
| 3 | Not run due to contamination in original sample - see Table I | | |
| 4 | 2 weeks | 10 | No Growth |
| 4 | 3 weeks | 10 | No Growth |
| 4 | 4 weeks | 1,800,000 | Gram Negative Bacilli |

The sample in each test was from a different tube. The tubes were kept in a freezer and were analyzed once a week.

TABLE III

| Example No. | Day 1 | 2 | 3 | 4 | 5 |
|---|---|---|---|---|---|
| After 2 weeks: | | | | | |
| 1 | 10 | 10 | 10 | 10 | 10 |
| 2 | 10 | 10 | 10 | 10 | 10 |
| 4 | 10 | 10 | 10 | 10 | 10 |
| After 4 weeks: | | | | | |
| 1 | 10 | 10 | 10 | 10 | 10 |
| 2 | 10 | 10 | 10 | 10 | 10 |
| 4 | 10 | 10 | 10 | 10 | 10 |

The samples for each test was from a different tube. The samples were kept at room temperature.

The sample of Example 3 was not run due to contamination in the original tubes.

TABLE IV

| Abuse Test - Samples at 37° C. | | | | | |
|---|---|---|---|---|---|
| | TPC | | | | |
| Example No. | Day 1 | Day 2 | Day 3 | Day 4 | Day 5 |
| Week 1 | | | | | |
| 1 | 10 | 10 | 51,000 | 2,600,000 | 3,800,000 |
| 2 | 10 | 10 | 10 | 10 | 10 |
| 4 | 10 | 10 | 10 | 54,000 | 70,000 |
| Week 2 | | | | | |
| 1 | 10 | 32,000 | 260,000 | 600,000 | 910,000 |
| 2 | 130,000 | 800,000 | discontinued | | |
| 4 | 10 | 10 | 10 | 10 | 10 |
| Week 3 | | | | | |
| 1 | 18,000 | 170,000 | discontinued | | |
| 2 | 10 | 10 | 10 | 10 | 10 |
| 4 | 130,000 | 1,600,000 | discontinued | | |

The sample for each test was from a different tube each week. The tubes were kept at 37° C.

The deep cleanser for normal to oily skin (cleanser oily) showed no growth right after being defrosted and the same goes for the moisturizer for normal to dry skin (day oily) as well as the moisturizing night cream for normal to oily skin (night cream oily). The moisturizer for oily skin (moisturizer oily) was immediately contaminated.

After two weeks at room temperature, the moisturizer oily was still contaminated and a contamination has taken place in the cleanser oily, even though, it was originally not contaminated. In the freezer, however, the cleanser oily sometimes shows contaminated tubes and sometimes clean tubes.

The night cream oily, which had remained clean during two weeks at room temperature, suddenly showed in one of the three analyzed tubes a high count when kept in the freezer.

All samples at room temperature, except the day oily which was discontinued, showed less than 10 for the first week.

In the second week at room temperature, the cleanser oily showed contamination and the day dry and night oily remained clean.

In the third week, at room temperature, all three samples remained clean.

In the abuse test in the oven, at 37° C. again the products go from a zero count to a high count in a rather erratic way and, it seems to show that there was already contamination in the unopened tube before being touched by the analyst.

The conclusion might be that for this kind of emulsion (oil in water), as sanitary as manufacturing on a production level might be, that there might always be the danger of contamination in at least some of the tubes and that the original deep freezing at $-100°$ C. might be able only to temporarily stop bacterial growth, as long as the product is still kept frozen.

The effect of pasteurization is shown by comparison of the actual plate count of a contaminated sample before and after pasteurization at 63° C. for 40 minutes.

| Ex No. | TPC before | TPC after | GS before | GS after |
|---|---|---|---|---|
| 1 | 1,200 |  | GNB | 0 per 0.1 g |
| 2 | 1,300 | NG | GNB | 0 per 0.1 g |
| 3 | 6,000 | NG | GNB | 0 per 0.1 g |
| 4 | 54,000 | NG | GNB | 0 per 0.1 g |

NG = No Growth
GNB = Gram Negative Bacilli

The effect of pasteurization at 63° C. for 40 minutes is shown by the following comparison at room temperature between tubes of the cream of Example 1 which had been pasteurized (P) and those which had not been pasteurized (U).

The TPC is as follows:

| Day 1 | P$^2$ | U | P$^3$ | U | P$^4$ | U | P$^5$ | U | P$^6$ | U | P$^7$ | U |
|---|---|---|---|---|---|---|---|---|---|---|---|---|
| 10 | 10 | 10 | 10 | 10 | 10 | 700 | 10 | 3.300,000 | 10 | 10 | 10 | 5,200,000 |

In each instance a different tube was used.

To test the effectiveness of pasteurization a water in oil (Example 1) and an oil in water emulsion (Example 2) sample was inoculated with 1,200,000 organisms per gram. The test organisms were:

| Bacterium - *S. aureus* | ATCC #6538 |
|---|---|
| Bacterium - *Ps. aeruginosa* | ATCC #9027 |
| Bacterium - *E. coli* | ATCC #8739 |
| Yeast - *C. albicans* | ATCC #10231 |

The 24 hour growths on T-Soy agar slants were removed with sterile isotonic saline. Serial dilutions of each suspension were made and plated to obtain colony levels. Tubes were immediately iced to prevent further bacterial growth. These cultures were diluted to yield 240,000,000/ml Equal quantities of the standard cultures were then blended.

A 20 gram portion of the test sample was transferred to a sterile screw-cap jar. 0.1 ml Of the mixed cultures was added and thoroughly blended to homogeneity. This yielded an inoculation of 1,200,000/g of product.

Within 15 minutes of the time of inoculation, a 1 gram portion was weighed into a sterile buffered Tween 80=Azolectin water blank from which serial dilutions were made for plating. The remainder of the inoculated material, in a tightly sealed sterile jar, was stored at 70°–72° F. for further analyses. The results are given under D in the Table below.

The samples obtained after inoculation were pasteurized at 62.8° C. for 40 minutes with the results under B in the Table. They were then frozen at $-70°$ C. on dry ice in an acetone bath with the results under C.

The sample obtained after freezing was kept frozen at $-20°$ C. and tested weekly with the results under $D_1$ to $D_4$ (4 weeks).

| Example No. | A | B | C | $D_1$ | $D_2$ | $D_3$ | $D_4$ |
|---|---|---|---|---|---|---|---|
| 1 | 1,200,000 | 20 | 10 | 10 | 10 | 10 | 10 |
| 2 | 1,200,000 | 10 | 10 | 10 | 10 | 10 | 10 |

Pasteurization and subsequent deep freezing brought down the count to less than 10. In the case of the water in oil emulsion, the count was 20 after pasteurization and went down to 10 after freezing illustrating the desirability of combining pasteurization and deep freezing.

A Use Test was performed whereby one tube of each of the formulations in Examples 1, 2 and 4 was kept at room temperature. Over small time intervals of 3 to 4 days portions were removed for plate count determination. The tubes were wiped with the technician's finger after each portion was squeezed out of the tube.

| Example No. | Day: 1 | 4 | 7 | 11 | 22 | 30 | 89 |
|---|---|---|---|---|---|---|---|
| 1 | 10 | 10 | 10 | 10 | 10 | 10 | 10 |
| 2 | 10 | 10 | 10 | 10 | 10 | 10 | 10 |
| 4 | 10 | 10 | 10 | 10 | 10 | 10 | 10 |

No contamination was found even after 5 months.

I claim:

1. A process for prolonging the shelf-life and the period of resistance to micro-organisms of cosmetics comprising:
   (a) subjecting said cosmetic to pasteurization while under vacuum or inert gas atmosphere by heating to a temperature of from about 60° C. to about 75° C. and
   (b) deep freezing said pasteurized cosmetic to a temperature of below about $-100°$ C.

2. A process according to claim 1, wherein said cosmetic consists solely of natural products.

3. A process according to claim 1, wherein said cosmetic contains a gum or gel.

4. A process according to claim 1, wherein said pasteurization is during a period of time ranging from about 45 to 50 minutes.

5. A process according to claim 1, wherein said pasteurization is at 62° or 63° C.

6. A process according to claim 1, wherein said cosmetic is incorporated in a final container for said cosmetic.

7. A process according to claim 6, wherein said container contains an elongated tubular dispensing nozzle for dispensing portions of said cosmetic.

8. A process according to claim 1, wherein said pasteurization is heated until the center of the cosmetic product is exposed to said temperature for at least 20 minutes.

9. A process according to claim 1, wherein before pasteurization said cosmetic is packed in airtight containers under vacuum or inert gas atmosphere.

10. A process for prolonging the shelf-life and the period of resistance to microorganisms of cosmetics comprising
   (a) subjecting said cosmetic comprising an oil-in-water emulsion to pasteurization while under vacuum or inert gas atmosphere by heating to a temperature of from about 60° C. to about 75° C. and
   (b) deep freezing said pasteurized cosmetic to a temperature of below about −100° C.

11. A process according to claim 10 wherein the cosmetically active part of said cosmetic consists solely of natural products.

* * * * *